United States Patent [19]

Fogarty

[11] Patent Number: 4,782,826

[45] Date of Patent: Nov. 8, 1988

[54] PENILE PROSTHESIS

[75] Inventor: Terence M. Fogarty, Hudson, Wis.

[73] Assignee: Mentor Corporation, Minneapolis, Minn.

[21] Appl. No.: 52,844

[22] Filed: May 21, 1987

[51] Int. Cl.⁴ .............................................. A61F 2/26
[52] U.S. Cl. ..................................................... 128/79
[58] Field of Search ......................................... 128/79

[56] References Cited

U.S. PATENT DOCUMENTS 4,566,466  1/1986  Fogarty ................................ 128/79

Primary Examiner—Robert Peshock
Assistant Examiner—Cary E. Stone
Attorney, Agent, or Firm—Kinney & Lange

[57] ABSTRACT

A penile implant includes an elongated member for implantation in the penis that is in fluid communication with a reservoir. The member includes an enclosure having a pressurizable chamber section such that the member is transformable between a flaccid and an erect state and a pump for transferring fluid from the reservoir to the pressurizable chamber. The pump has a valve portion made of a deformable material such that when the valve portion is deformed, fluid flows from the pressurizable chamber to the reservoir making the member flaccid. The valve portion is surrounded by a cushioning material to protect the valve portion from being accidentally deformed, permitting fluid to flow from the pressurizable chamber back to the reservoir.

21 Claims, 3 Drawing Sheets

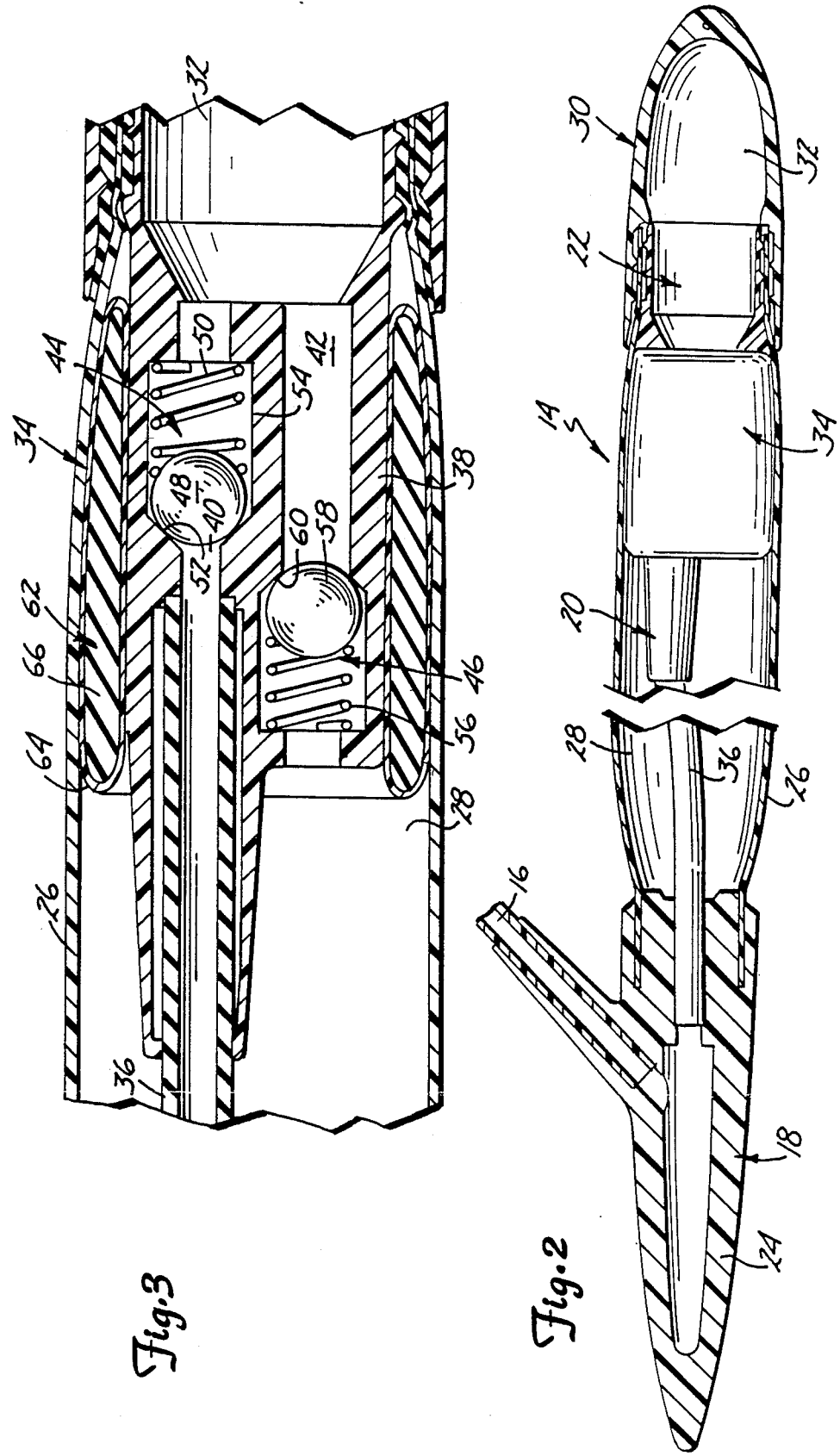

PENILE PROSTHESIS

BACKGROUND OF THE INVENTION

1. Field of the Invention.

The present invention relates to implants, and in particular, it relates to inflatable penile implants.

2. Description of the Prior Art.

There are generally two types of penile implants; one type is the solid-type implant as described in the Small et al U.S. Pat. No. 3,893,456, and the other type of implant is a hydraulic system that maintains a preselected working pressure in an elongated tubular member for an extended period of time. A number of such inflatable systems have been developed in recent years. Examples are described and illustrated in the following patents:

| United States Patent Documents | |
|---|---|
| Inventor | U.S. Pat. No. |
| Trick | 4,574,792 |
| Finney et al | 4,201,202 |
| Finney | 4,318,396 |
| Finney et al | 4,353,360 |
| Finney | 4,360,010 |
| Finney | 4,364,379 |
| Trick | 4,369,771 |
| Finney | 4,378,792 |
| Finney et al | 4,399,811 |
| Trick | 4,457,335 |
| Finney et al | 4,550,719 |
| Trick | 4,550,720 |
| Buuck | 3,954,102 |
| Burton et al | 4,267,829 |
| Scott et al | 4,383,525 |
| Burton et al | 4,407,278 |
| Porter et al | 4,590,927 |
| Whitehead | 4,399,812 |
| Strauch et al | 3,853,122 |
| Uson | 4,009,711 |
| Yamanaka | 4,235,227 |
| Fogarty | 4,537,183 |
| Fogarty | 4,566,446 |

| Foreign Patent Documents |
|---|
| PCT Appln. PCT/GB79/00130 |
| UK Patent 1174814 |

In one type of inflatable penile prosthesis, the pump and valving mechanism have been included in the elongated member that is implanted into the corpora cavernosa. Examples of such penile prostheses include the Porter et al U.S. Pat. No. 4,590,927, the Burton et al U.S. Pat. No. 4,407,278, the Scott et al U.S. Pat. No. 4,383,525, and the Trick U.S. Pat. No. 4,574,792. Placing the pump and valving mechanism in the penile cylinder provides a more accessible and more easily manipulable pump and valve mechanism.

SUMMARY OF THE INVENTION

The present invention includes a reservoir and enclosure adapted for implantation in fluid communication with the reservoir. The enclosure includes a pumping mechanism for pumping fluid from the reservoir to a pressurizable chamber such that the enclosure is transformable between a flaccid and an erect state. The pumping mechanism includes a valve portion made of a deformable material with the valve portion being surrounded by a cushioning material to prevent accidental release of the fluid from the pressurized chamber.

BRIEF DESCRIPTION OF THE DRAWINGS

FIG. 2 is a sectional view of the penile cylinder with portions show whole for purposes of clarity.

FIG. 3 is a sectional view of the valving portion of the pump of the present invention.

DETAILED DESCRIPTION OF THE PREFERRED EMBODIMENTS

Figure 1:
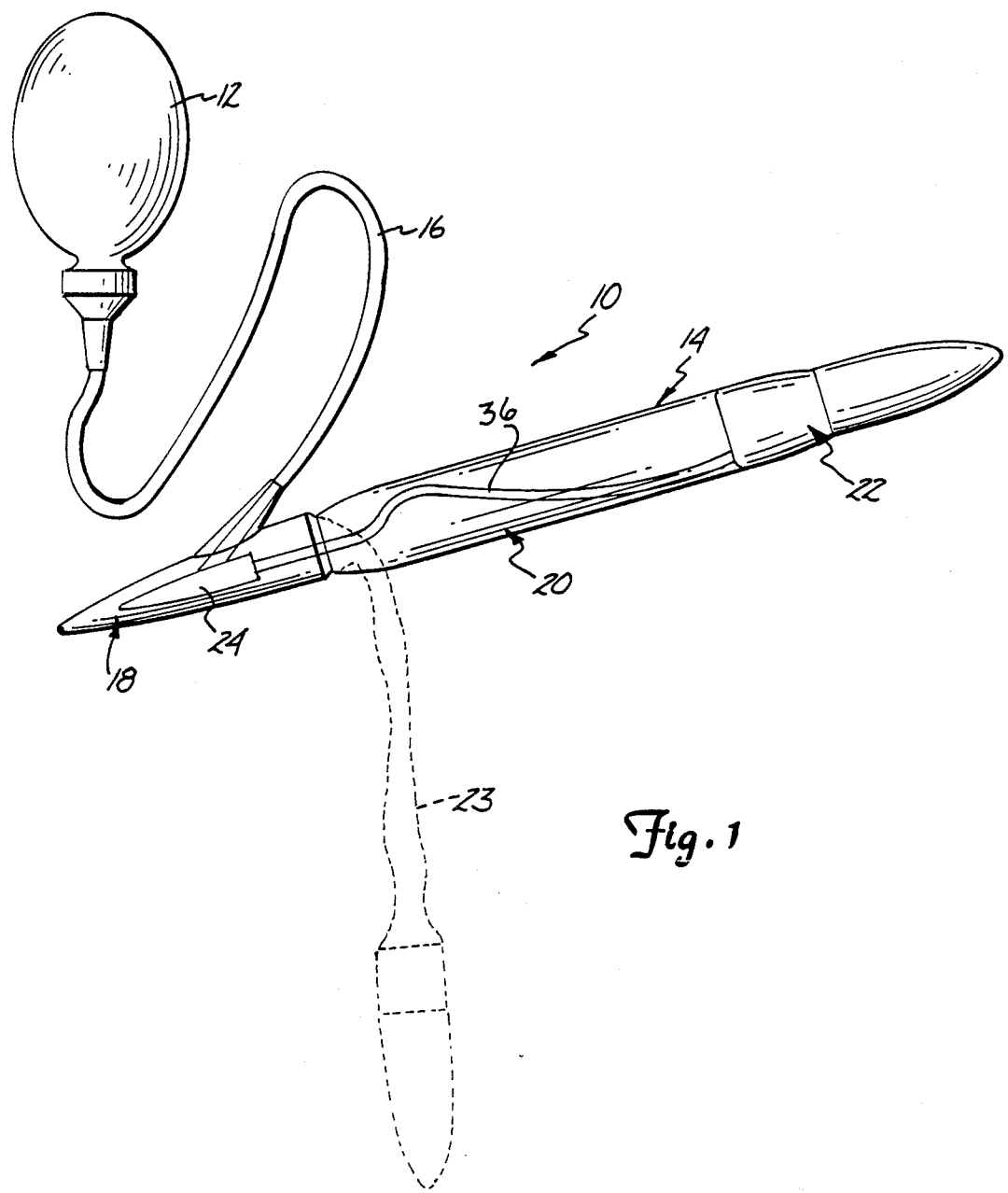
FIG. 1 is a perspective view of the penile implant of the present invention.

The present invention is generally indicated at 10 in FIG. 1. The device includes a fluid reservoir 12, an elongated member 14 fluidly connected to the reservoir 12 by tubing 16. The reservoir 12, the elongated member 14 and the tubing 16 are made of a medical grade material, such as silicone rubber or polyurethane elastomer.

The elongated member 14 includes a proximal end 18, an intermediate pressurizable chamber portion 20 and a pump section 22 located at a distal end on the member 14. As illustrated in FIGS. 1 and 2, the member 14 is in fluid communication with the reservoir 12 through the tubing 16. The proximal end portion 18 is made of a silicone rubber of a thickness and imparting a rigidity such that the proximal end 18 is non-expandable. The proximal end 18 includes a chamber or hollowed-out portion 24. The portion 24 is in fluid communication with the tubing 16. The portion 18 is of a size that is suitable for implantation in the crus of the penis, to support the intermediate and distal portion of the member 14.

The intermediate pressurizable chamber portion 20 includes a sleeve portion 26 that is attached to and extends from the proximal portion 18 forward to the distal end portion 22 and defines a chamber 28, as best illustrated in FIG. 2. The sleeve 26 is preferably made of a polyurethane elastomer and is sufficiently flexible so that when the chamber 28 is deflated. the device is transformed to a flaccid state, as indicated by broken lines 23 in FIG. 1.

The distal end portion 22 includes a pump bulb 30 having an interior pumping chamber 32 which is made of a medical grade silicone rubber. A polyurethane elastomer may also be used. The pump bulb 30 has a wall thickness that provides sufficient flexibility to the tip portion 22 so that it may be squeezed but prevents the tip portion from expanding or collapsing when under pressure. Preferably, the pump bulb 30 overlaps the sleeve 26 for approximately seven-sixteenths inch (7/16") in distance. The sleeve 26 and the portion 22 are attached to each other by a silicone adhesive.

The pump section 22 also includes a valve portion 34 disposed rearwardly of the pump bulb 30 and in fluid communication therewith. The valve portion 34 is in fluid communication with tubing 36. The tubing 36 extends through the chamber 28 and is connected to the proximal end portion 18 so that it is in fluid communication with the chamber 24. As clearly illustrated in FIG. 1, the tubing 36 is longer than the chamber 28 so that the tubing 36 does not restrict any longitudinal expansion of the chamber 28 that may occur upon inflation.

The valve portion 34 is more fully illustrated in FIG. 3. The valve portion 34 includes a valve housing 38. The valve housing 38 includes a first passage 40 that is in fluid communication with the tubing 36 at one end and with pumping chamber 32 at another end, and a second passage 42 in fluid communication with the pumping chamber at one end and the pressure chamber 28 at another end.

The valve portion 34 further includes first and second check valves 44 and 46, respectively. The check valve 44 includes a check ball 48 biased by a spring 50 against a valve seat 52 in a check valve housing 54 that is part of the passage 40. The valve seat 52 has a frusto-conical configured surface. Other seat configurations, such as spherical or flat, are also includable within the present invention. The spring 50 biases the check ball 48 against the seat 52 such that when the pump bulb 30 is squeezed and released, suction caused by the pump bulb 30 returning to its normal configuration will pull the check ball against the spring, away from the seat 52 to permit fluid to flow from the reservoir through the tubing 16, chamber 24, tubing 36 and valve passage 40 into the pumping chamber 32.

Similarly, the check valve 46 includes a spring 56 and a check ball 58. The spring 56 biases the check ball 58 against a valve seat 60. The valve seat 60 has a frusto-conical configurated surface. The ball 58 is biased in a direction opposite ball 48. The spring 56 biases the check ball 58 with a force sufficient to retain the check ball 58 against the seat while permitting fluid to flow from the pumping chamber 32 through the passage 42, unseating the check ball 58 and into the chamber 28. It will be appreciated that once the pump bulb 30 is released, the check ball 58 will be seated once again by the spring 56 against the valve seat 60.

The valve housing 30 is surrounded by a generally cylindrical gel pillow 62. In some embodiments, the gel pillow has an elliptical cross section. The gel pillow 62 includes an outer membrane 64 made of a silicone elastomer enclosing a silicone gel 66. The outer membrane may also be made of a polyurethane elastomer. The valve housing 34 is constructed of a highly elastic silicone elastomer so that it is easily deformable. The gel pillow 62 provides a cushion so that the valve housing is not accidentally released when squeezed with slight pressure, such as during intercourse. The gel pillow requires that the valve portion be positively and firmly grasped to release fluid from the chamber 28 back to the reservoir 12.

The gel pillow 62 extends from an end of the valve portion closest to the proximal end of the cylinder to a forward end of the valve portion closest to the pump 22. Preferably, the gel pillow extends completely around the valve portion not only to act as a cushion described above, but to make the cylinder soft in the valve portion area so that after implantation, the valve portion area feels more like the chamber portion 28 and the pump bulb portion 30.

The valve seats 52 and 60 are spaced apart along a longitudinal axis of the cylinder such that the valve seats lie on opposite sides of a plane perpendicular to such longitudinal axis. When squeezed, the valves are unseated by deformation along the longitudinal axis of the cylinder. As will be understood, the longitudinal deformation referred to it a component of the entire deformation that the valve portion undergoes when squeezed. The longitudinal deformation component is primarily responsible for unseating the check balls 48 and 50, permitting flow from the chamber 28 through the pump bulb 32, back to the reservoir. The offset position of the valve seats is the reason that the valve housing must be squeezed until it is sufficiently deformed longitudinally to unseat the check balls. The offset position of the valve seats further minimizes the chance that both check valves are released accidentally simultaneously.

Figure 4:
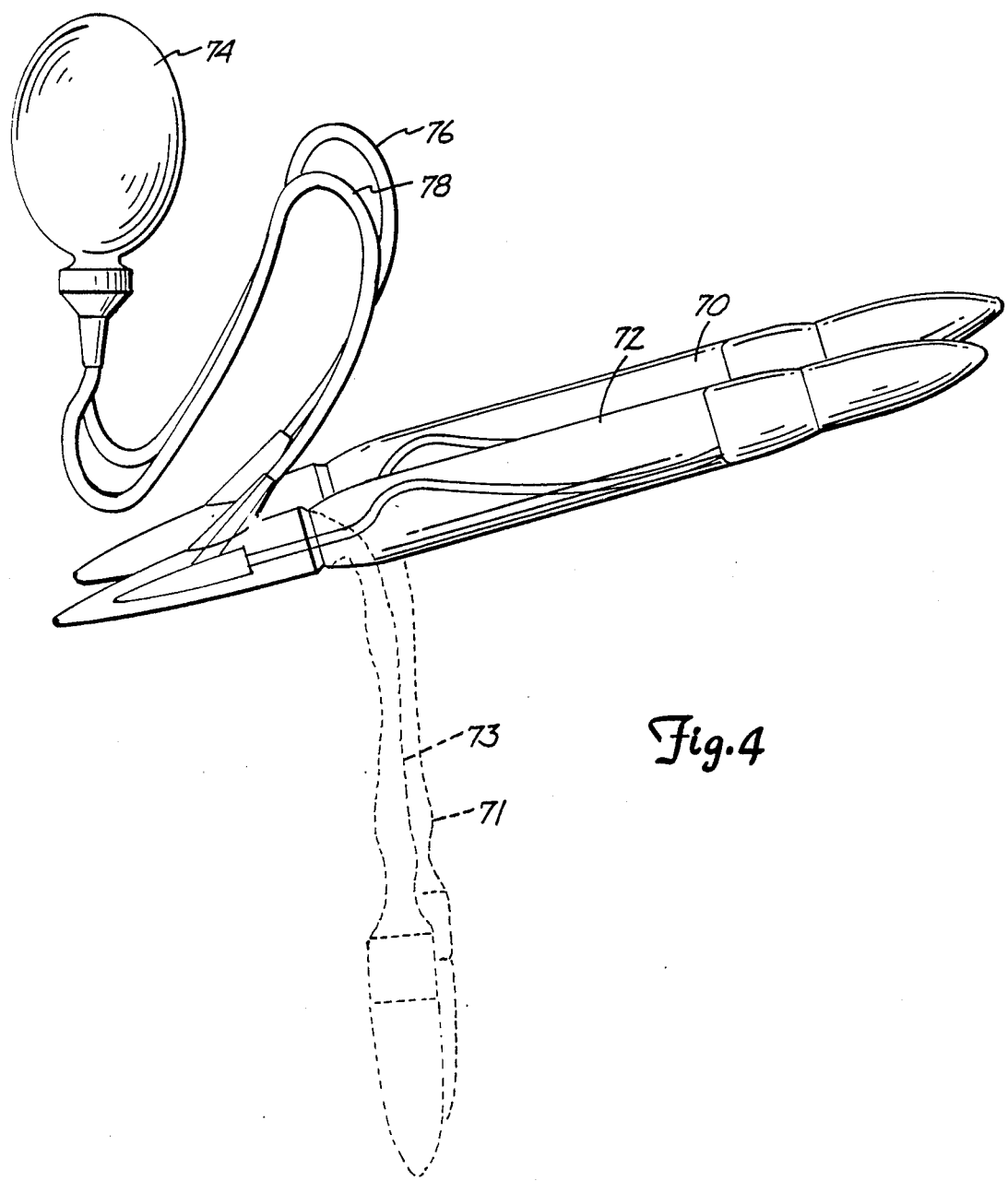
FIG. 4 is a perspective view of an alternative embodiment of the present invention.

Referring to FIG. 4, an alternative embodiment of the device of the present invention is illustrated. In the alternative embodiment, two penile prosthesis cylinders 70 and 72 are illustrated. The cylinders 70 and 72 are of the same construction as the cylinder 14 of FIGS. 1-3. The cylinders 70 and 72 are in fluid communication with a common reservoir 74 through tubing 76 and 78, respectively. Each cylinder 70 and 72 is operable independently of the other cylinder and is transformable from a flaccid state, as indicated by broken lines 71 and 73, to a pressurized state, such as indicated by the reference characters 70 and 72 in the same manner as cylinder 14 of FIGS. 1-3.

Although the present invention has been described with reference to preferred embodiments, workers skilled in the art will recognize that changes may be made in form and detail without departing from the spirit and scope of the invention.

What is claimed is:

1. A penile implant device in fluid communication with an implantable reservoir, the device comprising:
   a pressurizable cylinder adaptable for implantation, the cylinder including a pressurizable chamber and a means for pumping fluid from the reservoir to the pressurizable chamber, a deformable valving portion disposed within the cylinder, and cushioning means surrounding the valving portion whereby accidental deformation of the valving portion is minimized.

2. The device of claim 1 wherein the valving portion includes at least one biased check ball that is unseated when the valving portion is deformed.

3. The device of claim 2 wherein the valving portion includes two biased check balls that are unseated when the valving portion is deformed.

4. The device of claim 1 wherein the cushioning means includes a silicone gel enclosed by a silicone elastomer.

5. The device of claim 1 wherein the cushioning means includes a silicone gel enclosed by a polyurethane elastomer.

6. The device of claim 1 wherein the cushioning means includes a generally cylindrically configured cushioning material surrounding the valving portion.

7. The device of claim 6 wherein the cushioning means has an elliptical cross section.

8. The device of claim 1 wherein the means for pumping fluid is disposed within the cylinder.

9. The device of claim 1 wherein the valving portion includes two biased check balls, one check ball restricting flow between the chamber to the means for pumping fluid and the other check ball restricting flow between the reservoir to the means for pumping fluid, and a valve seat against which each check ball is biased, the valve seats being disposed on opposite sides of a plane perpendicular to a longitudinal axis of the cylinder such that the check balls are unseated primarily due to deformation of the valve portion along the longitudinal axis of the cylinder.

10. A penile implant device comprising:
    an implantable reservoir;
    first and second pressurizable cylinders adaptable for implantation, each cylinder in fluid communication with the reservoir, and each cylinder including a pressurizable chamber and a means for pumping fluid from the reservoir to the pressurizable chamber, a deformable valving portion disposed within each cylinder, and cushioning means surrounding the valving portion whereby accidental deformation of the valving portion is minimized.

11. The device of claim 10 wherein the valving portion of each cylinder includes at least one biased check ball that is unseated when the valving portion is deformed.

12. The device of claim 11 wherein the valving portion of each cylinder includes two biased check balls that are unseated when the valving portion is deformed.

13. The device of claim 10 wherein the cushioning means in each cylinder includes a silicone gel enclosed by a silicone elastomer.

14. The device of claim 10 wherein the cushioning means in each cylinder includes a silicone gel enclosed by a polyurethane elastomer.

15. The device of claim 10 wherein the cushioning means includes a cylindrical configured cushioning material surrounding the valve portion.

16. The device of claim 15 wherein the cushioning material has an elliptical cross section.

17. The device of claim 10 wherein the means for pumping fluid is disposed within each cylinder.

18. A penile implant device in fluid communication with an implantable reservoir, the device comprising:
a pressurizable cylinder adapted for implantation, the cylinder including a pressurizable chamber and a means for pumping fluid from the reservoir to the pressurizable chamber, a deformable valving portion disposed within the cylinder, the valving portion including two biased check balls, one check ball restricting flow between the chamber to the means for pumping fluid and the other check ball restricting flow between the reservoir to the means for pumping fluid, and a valve seat against which each check ball is biased, the valve seats being disposed on opposite sides of a plane perpendicular to a longitudinal axis of the cylinder such that the check balls are unseated primarily due to deformation of the valve portion along the longitudinal axis of the cylinder.

19. The device of claim 18 wherein the means for pumping fluid is disposed within the cylinder.

20. A penile implant device comprising:
an implantable reservoir;
first and second pressurizable cylinders adapted for implantation, each cylinder in fluid communication with the reservoir, and each cylinder including a pressurizable chamber and a means for pumping fluid from the reservoir to the pressurizable chamber, a deformable valving portion disposed within each cylinder, each valving portion including two biased check balls, one ball restricting flow between the chamber to the means for pumping fluid and the other check ball restricting flow between the reservoir to the means for pumping fluid, and a valve seat against which each check ball is biased, the valve seats being disposed on opposite sides of a plane perpendicular to the longitudinal axis of the cylinder such that the check balls are unseated primarily due to the deformation of the valve portion along the longitudinal axis of the cylinder.

21. The device of claim 20 wherein the means for pumping fluid is disposed within each cylinder.

* * * * *

UNITED STATES PATENT AND TRADEMARK OFFICE
CERTIFICATE OF CORRECTION

PATENT NO. : 4,782,826

DATED : November 8, 1988

INVENTOR(S) : Terence M. Fogarty

It is certified that error appears in the above-identified patent and that said Letters Patent is hereby corrected as shown below:

On the front page of the patent, in the References Cited section, under U.S. PATENT DOCUMENTS, insert the following references:

| | | | |
|---|---|---|---|
| — 4,360,010 | 11/1982 | Finney | 128/79 |
| 4,574,792 | 03/1986 | Trick | 128/79 |
| 4,364,379 | 12/1982 | Finney | 128/79 |
| 4,383,525 | 05/1983 | Scott et al | 128/79 |
| 4,353,360 | 10/1982 | Finney et al | 128/79 |
| 4,399,811 | 08/1983 | Finney et al | 128/79 |
| 4,550,719 | 11/1985 | Finney et al | 128/79 |
| 4,457,335 | 07/1984 | Trick | 137/552 |
| 4,369,771 | 01/1983 | Trick | 128/79 |
| 4,550,720 | 11/1985 | Trick | 128/79 |
| 3,853,122 | 12/1974 | Strauch et al | 128/79 |
| 4,009,771 | 03/1977 | Uson | 128/79 |
| 4,590,927 | 05/1986 | Porter et al | 128/79 — |

UNITED STATES PATENT AND TRADEMARK OFFICE
CERTIFICATE OF CORRECTION

PATENT NO. : 4,782,826

DATED : November 8, 1988

INVENTOR(S) : Terence M. Fogarty

It is certified that error appears in the above-identified patent and that said Letters Patent is hereby corrected as shown below:

(con't.)

-- 4,449,520   05/1984   Palomar et al..................128/79
   4,594,997   06/1986   Hakky.........................128/79
   4,572,168   02/1986   Fischell......................128/79
   4,399,812   08/1983   Whitehead.....................128/79 --.

Column 5, line 22, delete "valve" and insert --valving--.

Signed and Sealed this

Twenty-eighth Day of March, 1989

Attest:

DONALD J. QUIGG

Attesting Officer     Commissioner of Patents and Trademarks